(12) United States Patent
Prindle et al.

(10) Patent No.: US 11,007,352 B2
(45) Date of Patent: May 18, 2021

(54) BALLOON CATHETER

(71) Applicant: Boston Scientific Scimed, Inc., Maple Grove, MN (US)

(72) Inventors: Katherine M. Prindle, Robbinsdale, MN (US); Daniel James Horn, Shoreview, MN (US); Joel Munsinger, Blaine, MN (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 553 days.

(21) Appl. No.: 15/354,509

(22) Filed: Nov. 17, 2016

(65) Prior Publication Data

US 2017/0143943 A1 May 25, 2017

Related U.S. Application Data

(60) Provisional application No. 62/257,952, filed on Nov. 20, 2015.

(51) Int. Cl.
*A61M 25/10* (2013.01)
*A61M 25/09* (2006.01)

(52) U.S. Cl.
CPC ............ *A61M 25/10* (2013.01); *A61M 25/09* (2013.01); *A61M 25/1034* (2013.01);
(Continued)

(58) Field of Classification Search
CPC .. A61M 2025/1075; A61M 2025/1081; A61M 2025/1084; A61M 2025/1088;
(Continued)

(56) References Cited

U.S. PATENT DOCUMENTS 5,195,969 A * 3/1993 Wang ................ A61M 25/1029
604/103
5,409,495 A * 4/1995 Osborn .................... A61F 2/958
604/103.06
(Continued)

FOREIGN PATENT DOCUMENTS

JP 6507101 A 8/1994
JP 9507141 A 7/1997
(Continued)

OTHER PUBLICATIONS

International Search Report and Written Opinion for Application No. PCT/US2016/062527, 28 pages, dated Mar. 13, 2017.

*Primary Examiner* — Dianne Dornbusch
(74) *Attorney, Agent, or Firm* — Seager, Tufte & Wickhem LLP.

(57) ABSTRACT

Systems, devices, and methods including balloon catheters are described. In one embodiments, a balloon catheter assembly may comprise a tubular member having a proximal portion and a distal portion with a lumen extending between the proximal portion and the distal portion and a balloon member having a proximal waist portion, a distal waist portion, and an expandable region therebetween, the balloon member disposed proximate the distal portion of the tubular member and bonded to tubular member. The assembly may further comprise a first sleeve member covering a first portion of the tubular member and a portion of the balloon member proximal waist portion and a second sleeve member covering a second portion of the tubular member and a portion of the first sleeve member.

16 Claims, 10 Drawing Sheets

(52) U.S. Cl.
CPC .............. *A61M 2025/1075* (2013.01); *A61M 2025/1081* (2013.01); *A61M 2025/1084* (2013.01); *A61M 2025/1088* (2013.01)

(58) Field of Classification Search
CPC .............. A61M 25/10; A61M 25/1034; A61M 25/1002; A61M 25/1006; A61M 25/104; A61M 2025/1013; A61M 2025/1061; A61B 2017/22051; A61F 2/958; A61F 2002/9583; A61F 2002/9586
See application file for complete search history.

(56) References Cited

U.S. PATENT DOCUMENTS

| | | | |
|---|---|---|---|
| 5,445,646 A * | 8/1995 | Euteneuer | A61F 2/95 604/103.02 |
| 5,512,051 A * | 4/1996 | Wang | A61M 25/0045 604/101.02 |
| 5,536,252 A * | 7/1996 | Imran | A61M 25/1011 604/101.02 |
| 5,545,209 A * | 8/1996 | Roberts | A61F 2/958 604/103.05 |
| 5,810,871 A * | 9/1998 | Tuckey | A61F 2/958 606/108 |
| 5,968,069 A * | 10/1999 | Dusbabek | A61M 25/10182 606/194 |
| 6,136,258 A | 10/2000 | Wang et al. | |
| 6,174,316 B1 * | 1/2001 | Tuckey | A61F 2/958 606/108 |
| 6,264,683 B1 * | 7/2001 | Stack | A61F 2/958 623/1.11 |
| 6,443,980 B1 * | 9/2002 | Wang | A61F 2/958 623/1.11 |
| 6,482,348 B1 | 11/2002 | Wang et al. | |
| 6,565,595 B1 * | 5/2003 | DiCaprio | A61F 2/958 623/1.11 |
| 6,585,747 B1 * | 7/2003 | Limon | A61F 2/958 606/108 |
| 6,589,274 B2 * | 7/2003 | Stiger | A61F 2/958 606/192 |
| 6,726,714 B2 * | 4/2004 | DiCaprio | A61F 2/958 623/1.11 |
| 6,923,787 B2 | 8/2005 | Wang | |
| 6,982,024 B2 | 1/2006 | Shkolnik | |
| 7,691,224 B2 | 4/2010 | Weller et al. | |
| 7,708,931 B2 | 5/2010 | Schaeffer et al. | |
| 8,317,859 B2 * | 11/2012 | Snow | A61F 2/95 623/6.12 |
| 8,449,497 B2 | 5/2013 | Chen et al. | |
| 8,481,139 B2 | 7/2013 | Horn et al. | |
| 8,672,990 B2 | 3/2014 | Holman et al. | |
| 8,697,212 B2 | 4/2014 | Khieu et al. | |
| 2003/0135231 A1 * | 7/2003 | Goodin | B29C 65/00 606/192 |
| 2003/0138582 A1 | 7/2003 | Miller et al. | |
| 2003/0149399 A1 * | 8/2003 | Langan | A61M 25/10 604/103 |
| 2003/0191435 A1 * | 10/2003 | Shkolnik | A61M 25/1034 604/103 |
| 2003/0212360 A1 | 11/2003 | Shkolnik | |
| 2004/0062890 A1 * | 4/2004 | Wang | A61M 25/10 428/35.2 |
| 2006/0182907 A1 * | 8/2006 | Atanasoska | A61M 25/10 428/34.1 |
| 2006/0271091 A1 | 11/2006 | Campbell et al. | |
| 2009/0038752 A1 * | 2/2009 | Weng | A61M 25/10 156/276 |
| 2011/0064454 A1 | 3/2011 | Xu et al. | |
| 2011/0152764 A1 * | 6/2011 | Simpson | A61M 25/10 604/103 |
| 2015/0141917 A1 * | 5/2015 | Tilson | A61F 2/2433 604/103.07 |

FOREIGN PATENT DOCUMENTS

| | | |
|---|---|---|
| JP | 2004524057 A | 8/2004 |
| JP | 2008529656 A | 8/2008 |
| JP | 2008534032 A | 8/2008 |
| JP | 2009056297 A | 3/2009 |
| JP | 2009254626 A | 11/2009 |
| WO | 9219316 A1 | 11/1992 |
| WO | 9517920 A1 | 7/1995 |
| WO | 0222051 A2 | 3/2002 |
| WO | 2006086516 A2 | 8/2006 |

\* cited by examiner

BALLOON CATHETER

CROSS REFERENCE TO RELATED APPLICATIONS

This application claims the benefit of U.S. Provisional Patent Application Ser. No. 62/257,952 filed on Nov. 20, 2015, the disclosure of which is incorporated herein by reference.

TECHNICAL FIELD

The disclosure is directed to balloon catheter devices and methods for forming balloon catheters. More particularly, the disclosure is directed to balloon catheter devices and methods for bonding catheter balloons to catheter shafts.

BACKGROUND

Medical devices comprising catheter shafts and catheter balloons are used in an increasingly widening variety of applications including vascular dilatation, stent delivery, drug delivery, delivery and operation of sensors and surgical devices such as blades, and the like. The desired physical property profile for the balloons used in these devices varies according to the specific application, but for many applications a high strength robust balloon is necessary and softness and trackability properties are highly desirable. An application where high strength balloons, and more particularly balloons with high burst pressures, are useful is in the reopening of stenosis, for instance stenoses that develop at or in long-term shunts, ports or grafts employed for repeated blood access.

BRIEF SUMMARY

The disclosure is directed to several alternative designs, materials and methods of manufacturing medical device structures and assemblies, and uses thereof. In a first illustrative embodiment, a balloon catheter assembly may comprise a tubular member having a proximal portion and a distal portion with a lumen extending between the proximal portion and the distal portion and a balloon member having a proximal waist portion, a distal waist portion, and an expandable region therebetween, the balloon member disposed proximate the distal portion of the tubular member and bonded to tubular member. In at least some additional embodiments, the assembly may further comprise a first sleeve member covering a first portion of the tubular member and a portion of the balloon member proximal waist portion and a second sleeve member covering a second portion of the tubular member and a portion of the first sleeve member.

Additionally, or alternatively, in any of the embodiments according to the first illustrative embodiment, the first sleeve member may be in contact with the first portion of the tubular member and the portion of the balloon member proximal waist portion.

Additionally, or alternatively, in any of the embodiments according to the first illustrative embodiment, the first sleeve member may not cover any part of the second portion of the tubular member.

Additionally, or alternatively, in any of the embodiments according to the first illustrative embodiment, the second sleeve member may be in contact with the second portion of the tubular member and the portion of the first sleeve member.

Additionally, or alternatively, in any of the embodiments according to the first illustrative embodiment, the melting point of the first sleeve may be greater than the melting point of the second sleeve.

Additionally, or alternatively, in any of the embodiments according to the first illustrative embodiment, the second sleeve member may cover at least part of the first portion of the tubular member.

Additionally, or alternatively, in any of the embodiments according to the first illustrative embodiment, the assembly may further comprise a fiber layer disposed over the balloon member, the fiber layer may cover at least a portion of the balloon member proximal waist portion, and wherein the first sleeve further may cover a portion of the fiber layer.

Additionally, or alternatively, in any of the embodiments according to the first illustrative embodiment, the first sleeve member may be in contact with the fiber layer.

Additionally, or alternatively, in any of the embodiments according to the first illustrative embodiment, the balloon member may have a burst pressure greater than 1000 psi.

Additionally, or alternatively, in any of the embodiments according to the first illustrative embodiment, the first sleeve member may cover between 0.1 mm and 1.5 mm of the tubular member.

Additionally, or alternatively, in any of the embodiments according to the first illustrative embodiment, the first sleeve member may cover 0.5 mm of the tubular member.

Additionally, or alternatively, in any of the embodiments according to the first illustrative embodiment, the first sleeve member may cover between 2 mm and 5 mm of the balloon member proximal waist portion.

Additionally, or alternatively, in any of the embodiments according to the first illustrative embodiment, the first sleeve member may cover at least 3 mm of the balloon member proximal waist portion.

Additionally, or alternatively, in any of the embodiments according to the first illustrative embodiment, the first sleeve member may have a trapezoidal cross-section.

Additionally, or alternatively, in any of the embodiments according to the first illustrative embodiment, the first sleeve member may be longer along one edge than an opposite edge by between 0.25 mm and 1.75 mm.

Additionally, or alternatively, in any of the embodiments according to the first illustrative embodiment, the first sleeve member may be longer along one edge than an opposite edge by between 0.75 mm and 1.25 mm.

Additionally, or alternatively, in any of the embodiments according to the first illustrative embodiment, the second sleeve member may be between 0.5 mm to 5 mm long.

Additionally, or alternatively, in any of the embodiments according to the first illustrative embodiment, the second sleeve member may be between 1 mm to 2 mm long.

Additionally, or alternatively, in any of the embodiments according to the first illustrative embodiment, the second sleeve may cover between 0.1 mm and 1.5 mm of the tubular member.

Additionally, or alternatively, in any of the embodiments according to the first illustrative embodiment, the second sleeve may contact between 0.1 mm and 1.5 mm of the tubular member.

Additionally, or alternatively, in any of the embodiments according to the first illustrative embodiment, the second sleeve may cover 0.5 mm of the tubular member.

Additionally, or alternatively, in any of the embodiments according to the first illustrative embodiment, the second sleeve may contact 0.5 mm of the tubular member.

Additionally, or alternatively, in any of the embodiments according to the first illustrative embodiment, the second sleeve may cover between 0.1 mm and 1.5 mm of the first sleeve member.

Additionally, or alternatively, in any of the embodiments according to the first illustrative embodiment, the second sleeve may cover between 0.5 mm and 1 mm of the first sleeve member.

Additionally, or alternatively, in any of the embodiments according to the first illustrative embodiment, the first sleeve member may comprise a polyethylene terephthalate (PET) material.

Additionally, or alternatively, in any of the embodiments according to the first illustrative embodiment, the second sleeve member may comprise a polyether block amide (PEBA) material.

Additionally, or alternatively, in any of the embodiments according to the first illustrative embodiment, the first sleeve and the second sleeve comprise a single co-extruded sleeve.

In a second illustrative embodiment, a balloon catheter assembly may comprise a tubular member having a proximal portion and a distal portion with a lumen extending between the proximal portion and the distal portion and a balloon member having a proximal waist portion, a distal waist portion, and an expandable region therebetween, the balloon member disposed proximate the distal portion of the tubular member and bonded to the tubular member. In some additional embodiments, a first bond may bond the balloon member proximal waist portion to the tubular member, the first bond may comprise a first layer on top of the balloon member proximal waist portion and a second layer on top of the first layer. Additionally, at least a portion of the first layer may contact the tubular member, and at least a portion of the second layer may contact the tubular member.

Additionally, or alternatively, in any of the embodiments according to the second illustrative embodiment, at least a portion of the second layer may extend proximal of the proximal end of the first layer.

Additionally, or alternatively, in any of the embodiments according to the second illustrative embodiment, the melting point of the second layer may be lower than the melting point of the first layer.

Additionally, or alternatively, in any of the embodiments according to the second illustrative embodiment, the first layer may be in contact with the tubular member and the balloon member proximal waist portion.

Additionally, or alternatively, in any of the embodiments according to the second illustrative embodiment, the second layer may be in contact with the tubular member and the first layer.

Additionally, or alternatively, in any of the embodiments according to the second illustrative embodiment, the assembly further comprise a fiber layer disposed over the balloon member, the fiber layer may cover at least a portion of the balloon member proximal waist portion, and wherein the first layer may cover a portion of the fiber layer.

Additionally, or alternatively, in any of the embodiments according to the second illustrative embodiment, the first layer may be in contact with the fiber layer.

Additionally, or alternatively, in any of the embodiments according to the second illustrative embodiment, the balloon member may have a burst pressure greater than 1000 psi.

Additionally, or alternatively, in any of the embodiments according to the second illustrative embodiment, the first layer may cover between 0.1 mm and 1.5 mm of the tubular member.

Additionally, or alternatively, in any of the embodiments according to the second illustrative embodiment, the first layer may cover 0.5 mm of the tubular member.

Additionally, or alternatively, in any of the embodiments according to the second illustrative embodiment, the first layer may cover between 2 mm and 5 mm of the balloon member proximal waist portion.

Additionally, or alternatively, in any of the embodiments according to the second illustrative embodiment, the first layer may cover at least 3 mm of the balloon member proximal waist portion.

Additionally, or alternatively, in any of the embodiments according to the second illustrative embodiment, the second layer may be between 0.5 mm to 5 mm long.

Additionally, or alternatively, in any of the embodiments according to the second illustrative embodiment, the second layer may be between 1 mm to 2 mm long.

Additionally, or alternatively, in any of the embodiments according to the second illustrative embodiment, the second layer may cover between 0.1 mm and 1.5 mm of the tubular member.

Additionally, or alternatively, in any of the embodiments according to the second illustrative embodiment, the second layer may contact between 0.1 mm and 1.5 mm of the tubular member.

Additionally, or alternatively, in any of the embodiments according to the second illustrative embodiment, the second layer may cover 0.5 mm of the tubular member. Additionally, or alternatively, in any of the embodiments according to the second illustrative embodiment, the second layer may contact 0.5 mm of the tubular member.

Additionally, or alternatively, in any of the embodiments according to the second illustrative embodiment, the second sleeve may cover between 0.1 mm and 1.5 mm of the first layer.

Additionally, or alternatively, in any of the embodiments according to the second illustrative embodiment, the second sleeve may cover between 0.5 mm and 1 mm of the first layer.

Additionally, or alternatively, in further embodiments according to the second illustrative embodiment, the first layer of the first bond may comprise a polyethylene terephthalate (PET) material.

Additionally, or alternatively, in further embodiments according to the second illustrative embodiment, the second layer of first bond may comprise a polyether block amide (PEBA) material.

In a third illustrative embodiment, a method of bonding an expandable balloon onto a catheter shaft may comprise inserting a portion of a catheter shaft through an expandable balloon member, the expandable balloon member comprising a proximal waist portion, a distal waist portion, and an expandable region therebetween, positioning a first sleeve member over at least a portion of the balloon member proximal waist portion, and heating the first sleeve member. In some embodiments, the method may further comprise positioning a second sleeve member over at least a portion of the first sleeve member and heating the second sleeve member to bond the second sleeve member to the catheter shaft.

Additionally, or alternatively, in further embodiments according to the third illustrative embodiment, a first portion of the first sleeve member may be disposed directly over a portion of the catheter shaft and a second portion of the first sleeve member is disposed directly over the portion of the balloon member proximal waist portion.

Additionally, or alternatively, in further embodiments according to the third illustrative embodiment, a first portion of the second sleeve member may be disposed directly over a portion of the catheter shaft and a second portion of the second sleeve member may be disposed directly over the portion of the first sleeve member.

Additionally, or alternatively, in further embodiments according to the third illustrative embodiment, the first sleeve member and the second sleeve member may comprise a single, co-extruded sleeve member.

The above summary of some example embodiments is not intended to describe each disclosed embodiment or every implementation of the aspects of the disclosure.

BRIEF DESCRIPTION OF THE DRAWINGS

The aspects of the disclosure may be further understood in consideration of the following detailed description of various embodiments in connection with the accompanying drawings, in which.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Figure 1:
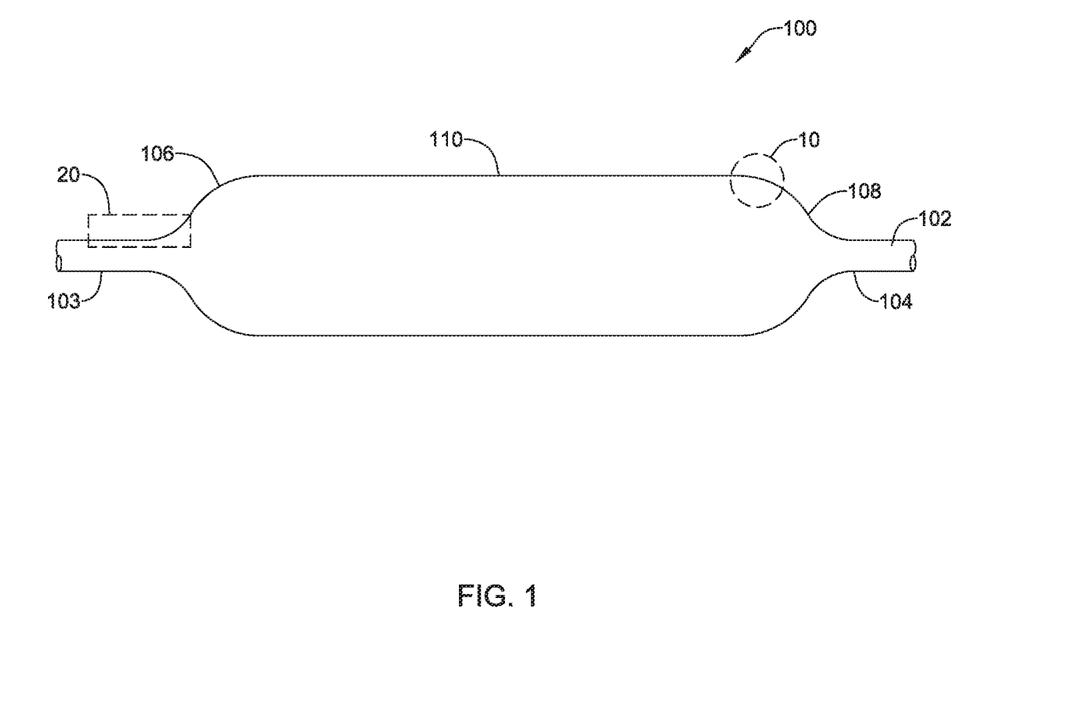
FIG. 1 is a perspective view of an exemplary balloon catheter in accordance with the disclosure.

FIG. 1 depicts exemplary balloon 100. Balloon 100 may be mounted onto shaft 102, and both balloon 100 and shaft 102 may be part of a larger catheter structure. In some embodiments, shaft 102 may have a length of about 20-250 cm and an outside diameter of approximately 1-10 French, depending upon the desired application. In some cases, shaft 102 may be part of a microcatheter that is adapted and/or configured for use within small anatomies of the patient. For example, shaft 102 and balloon 100 may be part of a catheter that is configured to navigate to target sites located in tortuous and narrow vessels such as, for example, to sites within the neurovascular system, certain sites within the coronary vascular system, or to sites within the peripheral vascular system such as superficial femoral, popliteal, or renal arteries. In some cases, the target site is a neurovascular site and may be located within a patient's brain, which is accessible only via a tortuous vascular path. However, it is contemplated that shaft 102 and balloon 100 may be used with catheters configured for use in other target sites within the anatomy of a patient. An exemplary catheter that may be utilized in accordance with the various embodiments as described herein is shown and described in U.S. Pat. No. 8,182,465, which is incorporated herein by reference in its entirety for all purposes.

Shaft 102 may include one or more lumens, for example a guidewire lumen and/or an inflation lumen. At least one lumen may terminate within balloon 100 to provide a conduit for inflation media to be delivered to and from balloon 100 in order to inflate and deflate balloon 100. Where shaft 102 includes a guidewire lumen, the guidewire lumen may run through balloon 100. In some embodiments, shaft 102 and balloon 100 may be delivered to a target site within a patient over a guidewire by sliding shaft 102 and balloon 100 over the guidewire.

Balloon 100 may generally comprise waist regions 103, 104, cone regions 106, 108 and body region 110. In some instances, balloon 100 may have an especially high burst pressure in order to be used in particular treatments, such as opening stenosed or otherwise obstructed arteries, vessels, or other lumens. However, it should be understood that the uses of the balloons and techniques of this disclosure are not limited to the specific use recited herein. The disclosed balloons and techniques may be useful in a multitude of situations.

Figure 2:
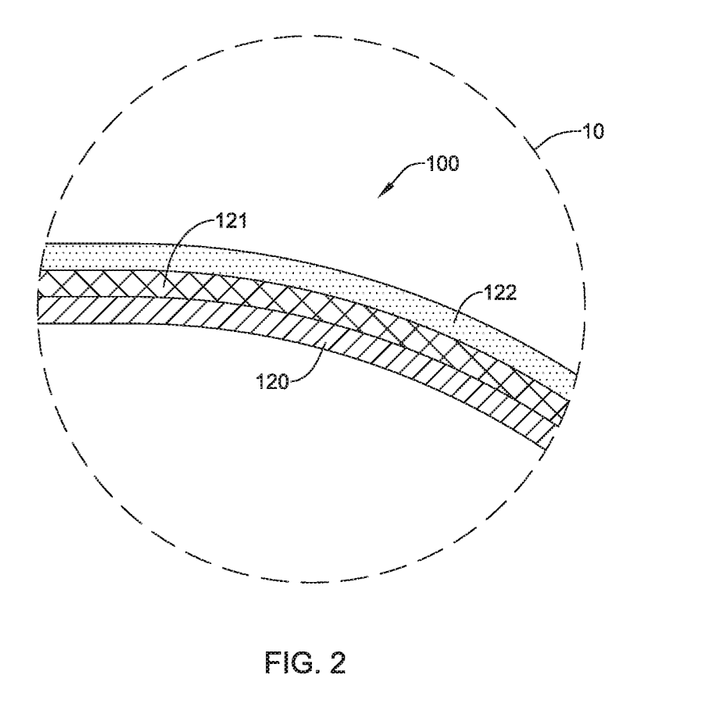
FIG. 2 is a cross-section of a region of the balloon of FIG. 1 depicting multiple layers of the balloon.

To achieve a high burst pressure, in some embodiments, balloon 100 may be a multi-layered balloon, as seen in FIG. 2. FIG. 2 depicts close-up of region 10 as depicted in FIG. 1, including a close-up of the structure of example balloon 100. As can be seen, balloon 100 may comprise multiple layers.

In some embodiments, balloon 100 may include at least base layer 120. Base layer 120 may be made from typical balloon materials such as one or more polymers (some examples of which are disclosed below), a metal-polymer composite, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. Of course, these are just a few exemplary materials. In general, base layer 120 may be comprised of any suitable polymer, copolymer, or curable material. In some instances, the base layer 120 may include a single layer of material, whereas in other instances base layer 120 may further comprise a multi-layer structure itself, including a plurality of layers of materials. For instance, base layer 120 may be formed as a co-extrusion or tri-layer extrusion in some instances.

In some embodiments, balloon 100 may further include fiber layer 121. Fiber layer 121 may be formed from any suitable technique to create a web pattern. For example, fiber layer 121 may be braided, woven, or wound in any different manner to create a web pattern. Additionally, fiber layer 121 may be formed from one, or multiple, of many different suitable materials. In general, the specific chosen material or materials, along with the specific chosen web pattern, can influence the distension properties of balloon 100. In some embodiments, fiber layer 121 may be formed separately from base layer 120 and later disposed over base layer 120. However, in other embodiments, fiber layer 121 may be formed directly over base layer 120. For example, the chosen material of fiber layer 121 may be woven or wound or otherwise formed into a web pattern directly over base layer 120.

Example suitable materials for fiber layer 121 include polyester, polyolefin, polyamide, polyurethane, liquid crystal polymer, polyimide, carbon, glass, mineral fiber or a combination thereof. Polyesters include polyethyleneterephthalate (PET), polybutylene terephthalate (PBT), and polytrimethylene terephthalate (PTT). Polyamides include nylons and aramids such as Kevlar®. Liquid crystal polymers include Vectran®. Polyolefins include ultrahigh molecular weight polyethylene, such as Dyneema,® sold by DSM Dyneema BVm Heerlen, Netherlands, Spectra® fibers, sold by Honeywell, and very high density polyethylene, and polypropylene fibers. Elastomeric fibers can be used in some cases. In some specific embodiments of the invention, the fibers are high strength materials which have a very low elongation and creep, such as aramid, liquid crystal polymer, or ultrahigh molecular weight polyethylene. Fibers comprising carbon nanotubes or carbon nanofibers may be suitable. Other carbon materials may also be suitable in some applications. It should be understood that these are only some example materials that may be suitable for use in fiber layer 121.

In some embodiments, as shown in FIG. 2, balloon 100 may include a top layer 122. However, top layer 122 may not be present in all embodiments. Where top layer 122 is included, top layer 122 may comprise a protective layer covering fiber layer 121. In some embodiments, top layer 122 may comprise a low-friction layer, which may allow balloon 100 to be advanced more readily through various body lumens.

Another factor aside from the addition of a fiber layer that can influence the burst pressure of balloon 100 is the bond between balloon 100 and shaft 102. For instance, in some embodiments, balloon 100 may be formed separately from shaft 102 and later bonded to shaft 102. In some embodiments, balloon 100 may generally comprise a distensible tube-like structure that is slid over shaft 102. Once in place, waist regions 103, 104 of balloon 100 may be bonded to shaft 102 to create a secure connection between balloon 100 and shaft 102. The specific materials used to create the bond, along with the specific process chosen to create the bond, can influence the burst pressure of balloon 100.

Figure 3:
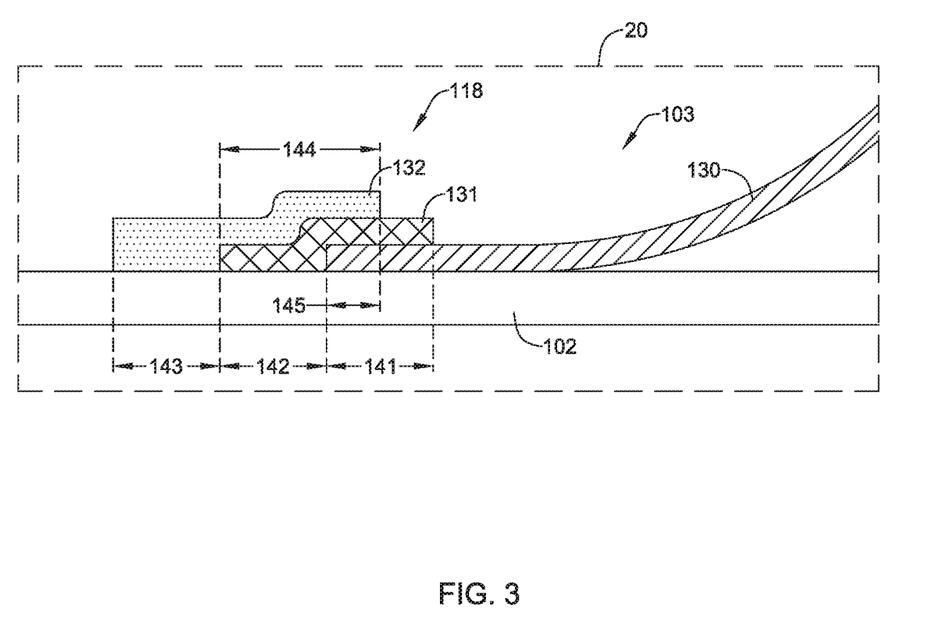
FIG. 3 is a partial cross-section of another region of the balloon of FIG. 1 depicting a bond securing the balloon to the shaft of FIG. 1.

FIG. 3 depicts one example bond that may be used to bond balloon 100 to shaft 102 in order to impart balloon 100 with a high burst pressure. Specifically, FIG. 3 depicts a close-up of region 20 of FIG. 1 including proximal balloon waist portion 103, with balloon 100 and layers 131, 132 of bond 118 shown in partial cross-section. Balloon wall 130 represents a cross-section of balloon 100 of FIG. 1. It should be understood that, although balloon wall 130 is only shown as a single layer, balloon wall 130 may represent the multi-layer structure depicted in FIG. 2. That is, even though balloon wall 130 is shown in FIG. 3 as a single layer, balloon wall 130 may include at least a base layer and a fiber layer as described with respect to FIG. 2.

In some embodiments according the present disclosure, bond 118 may comprise multiple layers in order to attach balloon wall 103 to shaft 102. First layer 131 may be comprised of a relatively high-temperature melting point material and may contact balloon wall 130 directly. Some example materials that may be suitable for first layer 131 include polyethylene terephthalate (PET) material, materials comprising polyimide, various fluoropolymers such as polytetrafluoroethylene (PFTE), perfluoroalkoxy alkane (PFA), fluorinated ethylene propylene (FEP), or still other materials.

In some embodiments, first layer 131 may directly cover, and may contact, at least a portion of balloon wall 130 proximate proximal balloon waist region 103 for a length 141. In different embodiments, length 141 may range between about 2 mm and about 5 mm. In more specific embodiments, length 141 may be about 2 mm, about 3 mm, about 4 mm, about 5 mm, or any other suitable length. In still further embodiments, length 141 may be greater than about 5 mm, such as between about 6 mm and about 10 mm, or even greater.

Additionally, in some embodiments, first layer 131 may extend proximally of balloon wall 130 to cover and contact at least a portion of shaft 102. For instance, first layer 131 may cover and/or contact shaft 102 for a length 142. Length 142 may range between about 0.1 mm and about 0.5 mm. In more specific embodiments, length 142 may be about 0.1 mm, about 0.2 mm, about 0.3 mm, about 0.4 mm, about 0.5 mm, or any other suitable value. In still other embodiments, length 142 may be greater than 0.5 mm, such as between about 0.6 mm and about 2 mm.

In further embodiments, bond 118 may also include second layer 132. Second layer 132 may have a relatively low-temperature melting point. For instance, second layer 132 may have a melting point temperature that is lower than at least the melting point temperature of first layer 131. Some example materials that second layer 132 may comprise include a polyether block amide (PEBA) material. One specific PEBA material is sold under the name PEBAX® 7233. However, it should be understood that other materials with the desired properties may also be used. In at least some embodiments, the material or materials used to form second layer 132 may be the same material or materials used to form balloon 100.

In some embodiments, second layer 132 may cover and directly contact at least a portion of first layer 131. For example, second layer 132 may cover and/or directly contact first layer 131 for a length 144. Length 144 may range between about 0.5 mm and about 2.5 mm. In more specific embodiments, length 144 may be about 0.5 mm, about 1.0 mm, about 1.5 mm, about 2.0 mm, about 2.5 mm, or any other suitable value.

In at least some embodiments that include second layer 132, second layer 132 may also cover at least a portion of balloon wall 130 in the proximal balloon waist region 103. In some embodiments, second layer 132 may not contact balloon wall 130 directly. Instead, second layer 132 may overlay at least a portion of first layer 131 that is in direct contact with balloon wall 130. Where second layer 132 covers at least a portion of balloon wall 130, second layer 132 may cover balloon wall 130 for a length 145. Length 145 may range between about 0.5 mm and about 2.5 mm. In more specific embodiments, length 145 may be about 0.5 mm, about 1.0 mm, about 1.5 mm, about 2.0 mm, about 2.5 mm, or any other suitable value.

In at least some embodiments, second layer 132 may extend proximal of first layer 131 and may contact shaft 102 directly. For instance, as shown in FIG. 3, second layer 132 may cover and contact shaft 102 directly for a length 143. In some embodiments, length 143 may range between about 0.1 mm and about 0.5 mm. In more specific embodiments, length 143 may be about 0.1 mm, about 0.2 mm, about 0.3 mm, about 0.4 mm, about 0.5 mm, or any other suitable value. In still other embodiments, length 143 may be greater than 0.5 mm, such as between about 0.6 mm and about 2 mm. In an example, second layer 132 may cover and/or directly contact balloon 103 distal of first layer 131. In some embodiments, second layer 132 may cover and/or directly contact balloon 103 distal of first layer 131 a length that may range between about 0.5 mm and about 2.5 mm. In more specific embodiments, second layer 132 may cover and/or directly contact balloon 103 distal of first layer 131 a length that may be about 0.5 mm, about 1.0 mm, about 1.5 mm, about 2.0 mm, about 2.5 mm, or any other suitable value.

Figure 4:
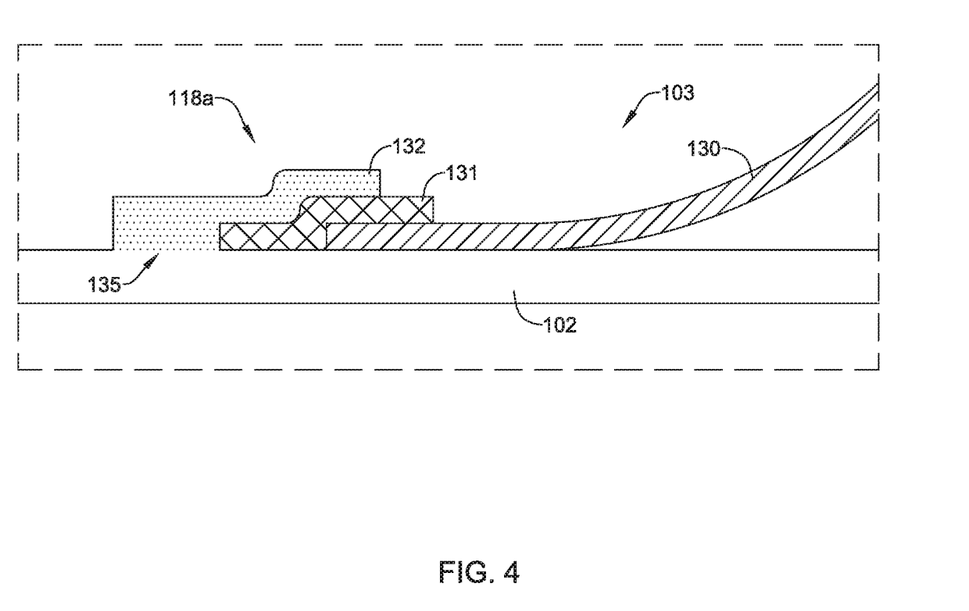
FIG. 4 is a partial cross-section of an alternative bond securing the balloon to the shaft of FIG. 1.

In order to create bond 118, first layer 131 and second layer 132 may be applied in separate steps. Heat may additionally be applied to shrink and compress layers 131 and/or 132 (and balloon wall 130 in proximal balloon waist region 103) around shaft 102 and/or to melt layers 131 and/or 132 to shaft 102. FIG. 4 depicts an example alternative structure of bond 118, bond 118a. In the example of FIG. 4, shaft 102 and second layer 132 may have similar melting points. As part of the bonding process, heat having a temperature greater than the melting points of shaft 102 and second layer 132 may be applied. This applied heat may cause the materials of shaft 102 and second layer 132 to flow together creating a secure connection between balloon wall 130 and shaft 102, as seen in region 135.

Figure 5:
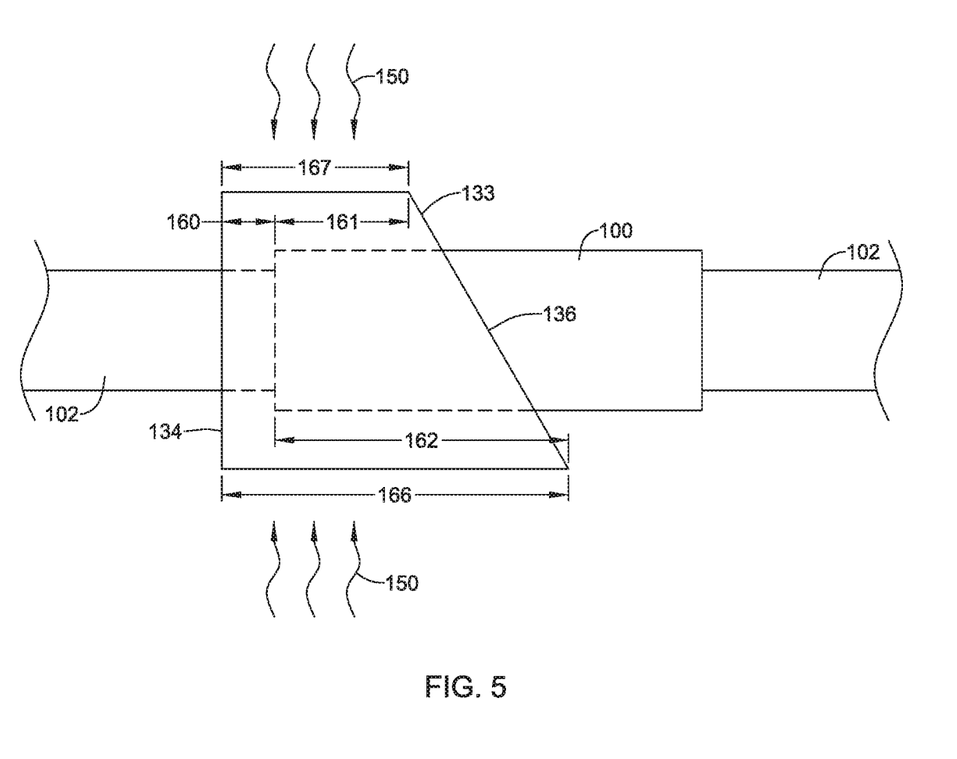
FIG. 5 depicts a step in the process of forming a bond of the present disclosure including positioning a sleeve over a balloon and a shaft.

FIGS. 5-8 depict an example process of forming bond 118 and/or 118a to secure balloon 100 to shaft 102. As mentioned previously, balloon 100 may be formed separately from shaft 102 and later slid onto shaft 102 for bonding. FIG. 5 depicts balloon 100 disposed on shaft 102 and in position for bonding. Once balloon 100 is in place on shaft 102, sleeve 133 may be slid over both shaft 102 and at least a portion of balloon 100.

In some embodiments, sleeve 133 may be used to create first layer 131 as described in FIGS. 3 and 4. For instance, sleeve 133 may comprise one or more of the materials described with respect to first layer 131. In some particular applications, sleeve 133 may have an inner diameter of about 2.2 mm and may have a wall thickness of about 0.013 mm. However, it should be understood these are example values only. In other embodiments, the inner diameter and wall thickness of sleeve 133 may be greater or less, depending on the specific size of shaft 102 and balloon 100.

Although not necessary in all embodiments, sleeve 133 may have a first straight edge 134 opposite a slanted or skived edge 136. As shown in FIG. 5, in profile, this may give sleeve 133 a trapezoidal shape. In some embodiments, sleeve 133 may have differing lengths along a top edge, as indicated by length 167, and a bottom edge, as indicated by length 166. In some embodiments, length 167 may range between about 2.5 mm and about 4.5 mm. In more specific embodiments, length 167 may be about 2.5 mm, about 3.0 mm, about 3.5 mm, about 4.0 mm, about 4.5 mm, or any other suitable value. Length 166 may range between about 4.0 mm and about 8.0 mm. In more specific embodiments, length 166 may be about 4.0 mm, about 5.0 mm, about 6.0 mm, about 7.0 mm, about 8.0 mm, or any other suitable value.

FIG. 5 shows sleeve 133 disposed about balloon 100 in a particular relation to balloon 100 and shaft 102. For instance, sleeve 133 may be disposed so that sleeve 133 covers shaft 102 for at least a length 160. Length 160 may correspond to length 142 described with respect to FIG. 3, as length 160 may represent the portion of sleeve 133 that covers and directly contacts shaft 102, forming layer 131.

Additionally, where sleeve 133 includes a slanted or skived edge 136, different portions of sleeve 133 may cover different lengths of balloon 100. For instance, along the top edge, or short portion, of sleeve 133, sleeve 133 may be disposed to cover balloon 100 for a length 161. Length 161 may range between about 2.0 mm and about 4.0 mm. In more specific embodiments, length 161 may be about 2.0 mm, about 2.5 mm, about 3.0 mm, about 3.5 mm, about 4.0 mm, or any other suitable value.

Along the bottom edge, or long portion, of sleeve 133, sleeve 133 may be disposed to cover shaft 102 for a length 162. Length 162 may range between about 3.5 mm and about 7.5 mm. In more specific embodiments, length 162 may be about 3.5 mm, about 4.5 mm, about 5.5 mm, about 6.5 mm, about 7.5 mm, or any other suitable value.

Once in place, heat may be applied to balloon 100, shaft 102, and sleeve 133, as represented by heat lines 150. The applied heat temperature may range between about 120 degrees Celsius and about 140 degrees Celsius. The heat may be applied by flowing air having the desired temperature flow over sleeve 133, shaft 102, and balloon 100. In some embodiments, the heat application may last between about 40 seconds and about 80 seconds. It should be understood that these values are only some examples. The specific temperature, time, and method of heat application may be different depending on the specific materials used and the desired properties of balloon 100. Additionally, alternative heating methods may be used, such as by use of a laser, heat-radiating metallic jaws, RF energy, or even other methods.

Figure 6:
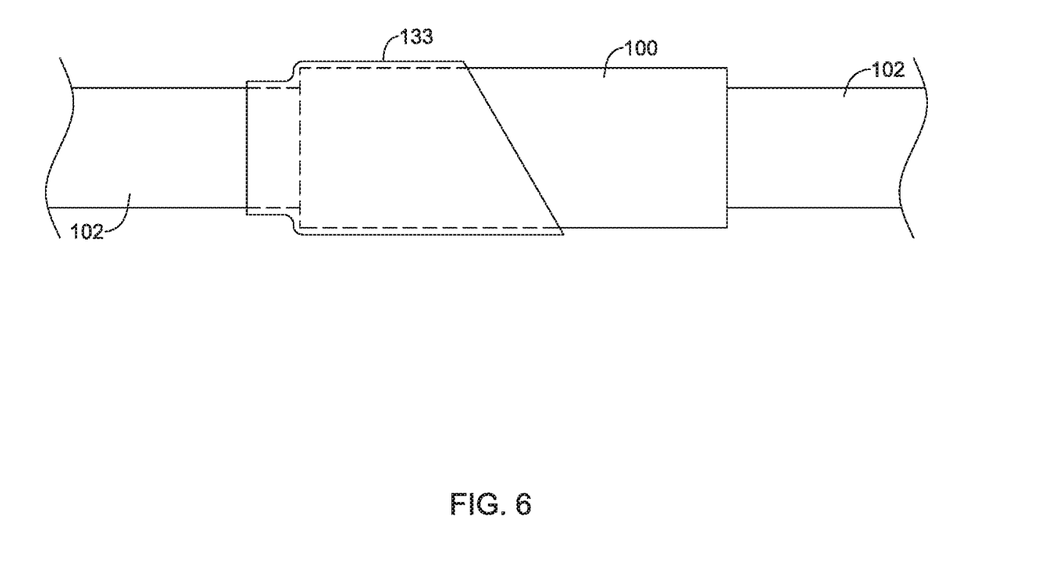
FIG. 6 depicts a result of applying heat to the sleeve of FIG. 5 to shrink the sleeve over the balloon and the shaft.

In general, the applied heat may be lower than the melting point of sleeve 133. Instead of melting, sleeve 133 may be configured to shrink under the application of heat. For instance, sleeve 133 may comprise a heat-shrink material. Accordingly, when the heat is applied, sleeve 133 may shrink down and compress balloon 100 against shaft 102 forming a first layer of a bond, such as first layer 131 of bond 118 of FIG. 3. FIG. 6 depicts sleeve 133 shrunk down and compressing balloon 100 against shaft 102.

Figure 7:
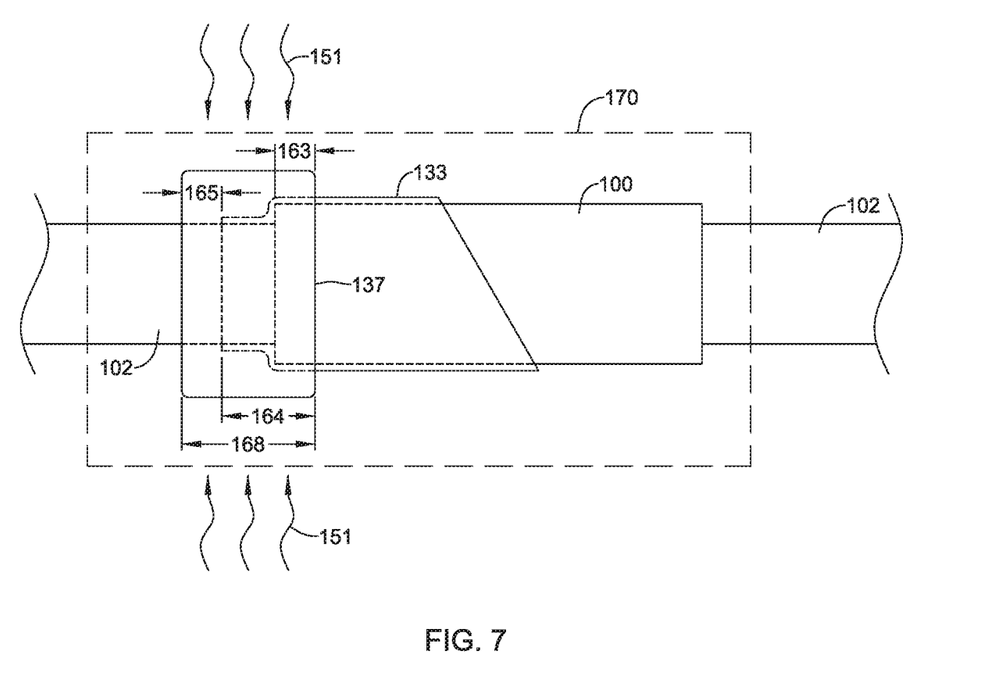
FIG. 7 depicts another step in the process of forming a bond of the present disclosure including positioning a second sleeve over a balloon, a shaft, and a first sleeve.

In some additional embodiments, after applying heat to shrink sleeve 133, a second sleeve, sleeve 137 of FIG. 7 may be positioned over first sleeve 133 and used to create a second layer of a bond, such as, for instance, bond 118 of FIG. 3. In some embodiments, second sleeve 137 may be used to create second layer 132 as described in FIGS. 3 and 4. For instance, sleeve 137 may comprise one or more of the materials described with respect to second layer 132. Sleeve 137 may have an overall length 168. In different embodiments, length 168 may be from between about 0.5 mm and about 5.0 mm. In more specific embodiments, length 168 may be about 0.5 mm, about 1.0 mm, about 1.5 mm, about 2.0 mm, about 3.0 mm, about 4.0 mm, about 5.0 mm, or any other suitable value.

FIG. 7 depicts sleeve 137 disposed about balloon 100, shaft 102, and sleeve 133 in relation to those other components. For instance, sleeve 137 may be disposed so that sleeve 137 covers shaft 102 for at least a length 165. Length 165 may correspond to length 143 described with respect to FIG. 3, as length 165 may represent the portion of sleeve 137 that covers and directly contacts shaft 102 in the final bond. Additionally, sleeve 137 may be disposed so that sleeve 137 covers sleeve 133 for a length 164. In different embodiments, length 164 may range between about 0.2 mm and about 2 mm. In more specific embodiments, length 164 may be about 0.2 mm, about 0.3 mm, about 0.4 mm, about 0.5 mm, about 1.0 mm, about 2.0 mm, or any other suitable value.

In some additional embodiments, sleeve 137 may further cover a portion of balloon 100. For example, as shown in FIG. 7, sleeve 137 may cover a length 163 of balloon 100. Generally, in some embodiments, sleeve 137 may cover sleeve 133, which in turn covers balloon 100.

In different embodiments, length 163 may range between about 0.1 mm and about 1.0 mm. In more specific embodiments, length 163 may be about 0.1 mm, about 0.2 mm, about 0.3 mm, about 0.4 mm, about 0.5 mm, about 0.6 mm, about 0.8 mm, about 1.0 mm, or any other suitable value. However, in still other embodiments, sleeve 137 may not cover any of balloon 100. Accordingly, in some embodiments, there would be no applicable length 163.

Once sleeve 137 has been disposed in the desired position, heat may be applied to sleeve 137 and in the corresponding region around sleeve 137, as represented by heat lines 151. In some embodiments, there may be a two-stage heat application. For instance, in a first stage, heated air similar to that described with respect to FIG. 5 may again be applied once sleeve 137 is in place.

In the second stage, sleeve 137 and the other components in the corresponding region around sleeve 137 may be placed in a hot-jaws apparatus. The hot-jaws apparatus may comprise two semi-circular components that, when brought together, form a lumen. In some specific embodiments, the lumen of the hot-jaws apparatus may have an inner diameter in the range of about 2.5 mm. However, this is just one example dimension. Other sized hot-jaws may be used in conjunction with shafts and balloons that are smaller or larger.

Heat may then be applied to the jaws to deliver heat to a localized area (e.g. within the lumen of the jaws). Shaft 102 and balloon 100 may be positioned within the hot-jaws so that sleeve 137 is disposed within the lumen of the hot-jaws. In this manner, heat may be applied locally to sleeve 137 and the region around sleeve 137.

In some embodiments, the hot-jaws apparatus may be heated to between about 220 degrees Celsius and about 300 degrees Celsius. Sleeve 137 may be placed between the halves of the hot-jaws apparatus for between about 15 seconds and about 40 seconds. In at least some embodiments, this temperature may be above the melting point temperature of sleeve 137, and the time of application may be sufficient to cause sleeve 137 to melt. This melting may securely attach sleeve 137 to shaft 102 and sleeve 133.

In at least some additional embodiments, the temperature of the hot-jaws may also be above the melting point temperature of shaft 102. Accordingly, in some embodiments, while in the hot-jaws, shaft 102 may also melt. This reflow of both shaft 102 and of sleeve 137 may allow for mixing of the materials between shaft 102 and sleeve 137 to create a strong bond between sleeve 137 and shaft 102.

Although not necessary in all embodiments, before applying heat to sleeve 137 and the corresponding region around sleeve 137, a protective heat-shrink layer may be positioned over sleeve 137, as represented by dashed box 170 in FIG. 7. In some embodiments, after heat application by the jot-jaws apparatus, this protective heat-shrink layer may be removed, resulting in the structure depicted in FIG. 8. In some embodiments, the resulting bond depicted in FIG. 8 may have a length 191 and a width or diameter 193. In some embodiments, length 191 may be about 2.0 mm and width 193 may be about 2.0 mm. However, in other embodiments, length 191 and/or width 193 may be greater or less than 2.0 mm depending on the size of shaft 102 and balloon 100, and possibly the ultimate desired properties of balloon 100.

Figure 8:
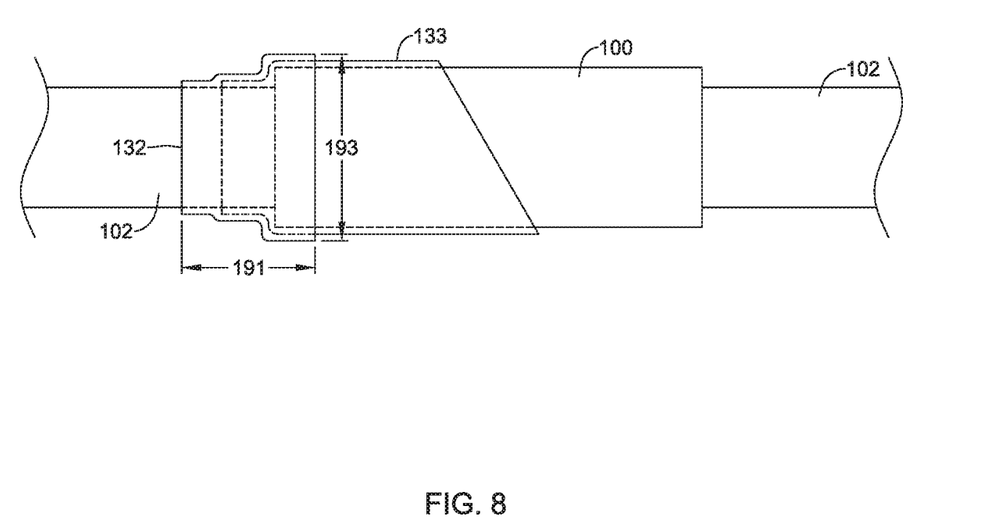
FIG. 8 depicts a result of applying heat to the second sleeve of FIG. 7 to shrink and/or melt the second sleeve over the balloon, the shaft, and the first sleeve.

The bond depicted in FIG. 8 and other figures of this disclosure may allow balloon 100 to withstand high pressures in the range of 500 psi to 1500 psi, and more specifically in the range of 750 psi to 1250 psi. Pressures in these ranges may make balloon 100 suitable for use in a variety of applications for which balloons that burst under lower pressures would not be suited, such as for opening certain types of strictures within vessels or body lumens.

Additionally, although FIGS. 2-8 only depict balloon 100 bonded to shaft 102 along proximal balloon waist portion 103, in some embodiments, balloon 100 may also be bonded to shaft 102 in a similar manner along distal balloon waist portion 104. In this manner, both ends of balloon 100 may be bonded to shaft 102 in accordance with the techniques disclosed herein to produce a balloon that can withstand high internal pressures.

Figure 9A:
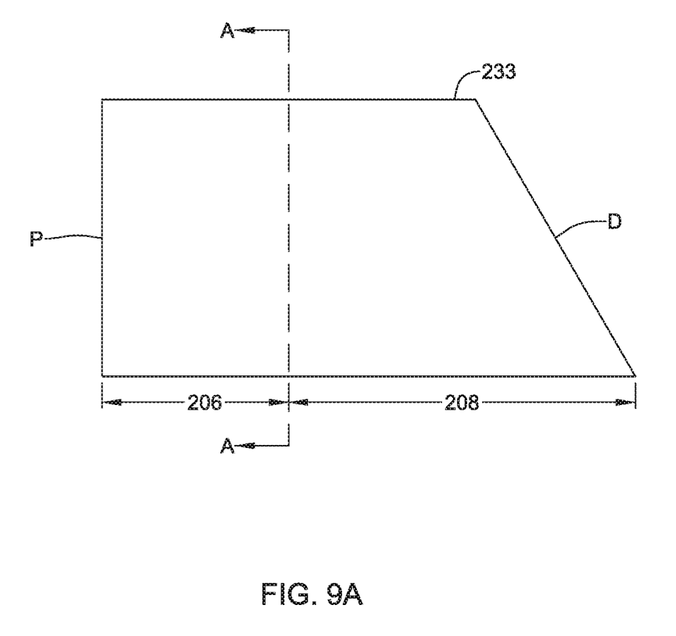
FIG. 9A depicts an example co-extruded sleeve that may be used to form any of the bonds of the present disclosure.
Figure 9B:
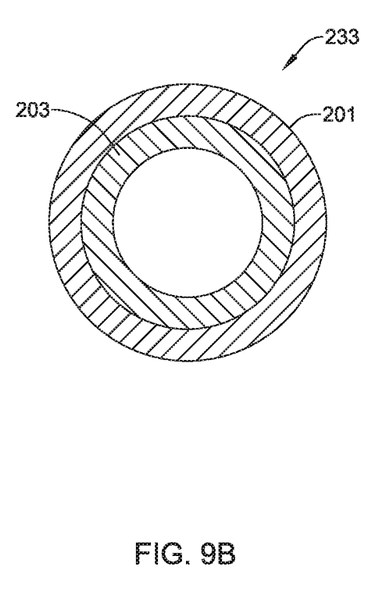
FIG. 9B is a cross-sectional view of the co-extruded sleeve of FIG. 9A taken along line A-A.

FIGS. 9A-B depict example co-extruded sleeve 233 that may be used to form any of the bonds described in the present disclosure, for instance bond 118. In at least some embodiments, sleeve 233 may be similar to sleeve 133 described with respect to FIG. 5. For instance, sleeve 233 may have similar shape and be of a similar size and length as sleeve 133. However, in the example of FIGS. 9A-B, sleeve 233 may be a co-extruded sleeve comprising multiple layers of different materials instead of a comprising a single layer of material. As can be seen in FIG. 9B, sleeve 233 may comprise at least two separate layers, outer layer 201 and inner layer 203. Inner layer 203 may comprise a material similar to those materials described with respect to sleeve 133. Outer layer 201 may comprise a material similar to those materials described with respect to sleeve 137 in FIG. 7.

In embodiments where sleeve 233 is used to form a bond such as bond 118, only a single sleeve, sleeve 233, may be used to form the bond. For example, referring to FIG. 5, once balloon 100 has been disposed about shaft 102 at the desired location, sleeve 233 may be positioned over balloon 100 as shown in FIG. 5. As with sleeve 133, heat may be applied to sleeve 233 to shrink sleeve 233 down onto balloon 100 and shaft 102. Afterwards, balloon 100, shaft 102, and sleeve 233 may undergo further heating, such as by being placed in a hot-jaws apparatus. The additional heating by the hot-jaws apparatus may cause outer layer 201 to melt while inner layer 203 remains un-melted. As outer layer 201 melts, a portion of outer layer 201 may flow proximally beyond proximal edge P of sleeve 233 and onto shaft 102. Once the heat is removed, the melted portion of outer layer 201 may solidify to shaft 102 at a point proximal of inner layer 203 and covers shaft 102, resulting in bond 118 depicted in FIGS. 3 and/or 4. In this manner, a single sleeve may form bond 118, which may reduce the complexity of the process used to form bond 118.

In at least some of embodiments of sleeve 223, only a portion of sleeve 233 may be a co-extrusion. For instance, outer layer 201 and inner layer 203 may only be coextruded along a proximal portion 206 of sleeve 223, with only inner layer 203 extending along distal portion 208 toward distal edge D of sleeve 223. In at least some embodiments, proximal portion 206 may have a length that is similar to the lengths described for sleeve 137 above.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed:

1. A balloon catheter assembly comprising:
   a tubular member having a proximal portion and a distal portion with a lumen extending between the proximal portion and the distal portion;
   a balloon member having a proximal waist portion, a distal waist portion, and an expandable region therebetween, the balloon member disposed proximate the distal portion of the tubular member and bonded to the tubular member;
   a first sleeve member covering and in direct contact with a first portion of the tubular member and a portion of the balloon member proximal waist portion, wherein a distal end of the first sleeve member is in direct contact with and bonded to the balloon member proximal waist portion; and
   a second sleeve member covering and in direct contact with a second portion of the tubular member and a portion of the first sleeve member, wherein a distal end of the second sleeve member is positioned proximal of the distal end of the first sleeve member.

2. The balloon catheter of claim 1, wherein the second sleeve member does not contact the balloon member directly.

3. The balloon catheter of claim 1, wherein a melting point of the first sleeve is greater than a melting point of the second sleeve.

4. The balloon catheter of claim 1, wherein the second sleeve member covers at least part of the first portion of the tubular member.

5. The balloon catheter of claim 1, wherein the balloon member includes a fiber layer in at least a portion of the balloon member proximal waist portion, and wherein the first sleeve further covers a portion of the fiber layer.

6. The balloon catheter of claim 5, wherein the first sleeve member is in contact with the fiber layer.

7. The balloon catheter of claim 5, wherein the balloon member has a burst pressure greater than 1000 psi.

8. The balloon catheter of claim 1, wherein the first sleeve member covers between 0.1 mm and 1.5 mm of the tubular member.

9. The balloon catheter of claim 1, wherein the second sleeve member is between 0.5 mm to 5 mm long.

10. The balloon catheter of claim 1, wherein the first sleeve member comprises a polyethylene terephthalate (PET) material.

11. The balloon catheter of claim 1, wherein the second sleeve member comprises a polyether block amide (PEBA) material.

12. A balloon catheter assembly comprising:
    a tubular member having a proximal portion and a distal portion with a lumen extending between the proximal portion and the distal portion;
    a balloon member having a proximal waist portion, a distal waist portion, and an expandable region therebetween, the balloon member disposed proximate the distal portion of the tubular member and bonded to the tubular member;
    a first bond bonding the balloon member proximal waist portion to the tubular member, the first bond comprising a first layer on top of the balloon member proximal waist portion and a second layer on top of the first layer,
    wherein at least a portion of the first layer directly contacts the tubular member, and a distal end of the first layer directly contacts and is bonded to the balloon member proximal waist portion,
    wherein at least a portion of the second layer directly contacts the tubular member; and
    wherein a distal end of the second layer is positioned proximal of the distal end of the first layer.

13. The balloon catheter of claim 12, wherein at least a portion of the second layer extends proximal of a proximal end of the first layer.

14. The balloon catheter of claim 12, wherein a melting point of the second layer is lower than a melting point of the first layer.

15. The balloon catheter of claim 12, wherein the first layer of the first bond comprises a polyethylene terephthalate (PET) material.

16. The balloon catheter of claim 12, wherein the second layer of first bond comprises a polyether block amide (PEBA) material.

\* \* \* \* \*